United States Patent
Pullen et al.

(10) Patent No.: US 11,957,549 B2
(45) Date of Patent: Apr. 16, 2024

(54) APPENDAGE GARMENT WITH ENHANCED TRACTION

(71) Applicant: LZRD Tech, Inc., Atlanta, GA (US)

(72) Inventors: Michael Pullen, Cream Ridge, NJ (US); Mathew Quon, Rose Valley, PA (US); Jud Ready, Atlanta, GA (US)

(73) Assignee: LZRD Tech, Inc., Atlanta, GA (US)

( * ) Notice: Subject to any disclaimer, the term of this patent is extended or adjusted under 35 U.S.C. 154(b) by 29 days.

(21) Appl. No.: 17/636,615

(22) PCT Filed: Aug. 21, 2020

(86) PCT No.: PCT/US2020/047423
§ 371 (c)(1),
(2) Date: Feb. 18, 2022

(87) PCT Pub. No.: WO2021/035148
PCT Pub. Date: Feb. 25, 2021

(65) Prior Publication Data
US 2022/0296429 A1  Sep. 22, 2022

Related U.S. Application Data

(60) Provisional application No. 62/890,109, filed on Aug. 22, 2019.

(51) Int. Cl.
*A41D 13/08* (2006.01)
*A41D 27/10* (2006.01)
(Continued)

(52) U.S. Cl.
CPC .............. *A61F 13/08* (2013.01); *A41D 13/08* (2013.01); *A41D 27/10* (2013.01); *A41D 27/085* (2013.01)

(58) Field of Classification Search
CPC ........ A63B 71/12; A41D 13/08; A41D 27/10; A41D 13/0156; A41D 13/015;
(Continued)

(56) References Cited

U.S. PATENT DOCUMENTS 2,552,177 A * 5/1951 Hurt ...................... A41D 13/08
2/24
3,322,118 A * 5/1967 Sotherlin .............. A61F 13/069
2/24
(Continued)

FOREIGN PATENT DOCUMENTS

| CN | 104772955 A | 7/2015 | |
|---|---|---|---|
| CN | 211153875 U | 8/2020 | |
| WO | WO-2018066504 A1 * | 4/2018 | ............... A41D 1/06 |

OTHER PUBLICATIONS

English machine translation of WO 2018066504 A1. Via espacenet.com. Translation performed on Feb. 2, 2023. (Year: 2018).*
(Continued)

*Primary Examiner* — Jameson D Collier
(74) *Attorney, Agent, or Firm* — Troutman Pepper Hamilton Sanders LLP

(57) ABSTRACT

A multifunctional piece of athletic and/or work wear is presented. When worn as a compression sleeve to play rugby, American football and other ball-carrying sports (with oblong or round balls), or when worn to carry objects during physical labor, an object contact surface positioned on the inner forearm of the sleeve can grip the carried object with increased friction while an outside facing surface of the sleeve can be smooth to deflect defenders or objects that may impact the sleeve, can be padded to protect from impacts, can provide protection from contusions and lacerations, and/or can provide active cooling. The garment can further (Continued)

include static or dynamic readable symbols or images woven or knitted into the garment (rather than printed or fused onto the garment).

12 Claims, 5 Drawing Sheets

(51) Int. Cl.
*A61F 13/08* (2006.01)
*A41D 27/08* (2006.01)

(58) Field of Classification Search
CPC .... A41D 13/0005; A41D 13/06; A41D 31/18; A41D 2400/80
USPC ........................ 2/16, 22, 24, 59, 125; 602/63
See application file for complete search history.

(56) References Cited

U.S. PATENT DOCUMENTS

| | | | |
|---|---|---|---|
| 4,150,442 A * | 4/1979 | Boone | A41D 13/08 2/24 |
| 4,756,026 A | 7/1988 | Pierce, Jr. | |
| 4,951,317 A | 8/1990 | Gray et al. | |
| 5,023,953 A | 6/1991 | Bettcher | |
| 5,168,577 A * | 12/1992 | Detty | A41D 13/065 2/24 |
| 5,210,877 A | 5/1993 | Newman | |
| 5,210,878 A | 5/1993 | Triche | |
| 5,367,708 A | 11/1994 | Fujimoto | |
| 5,418,980 A * | 5/1995 | Kelly | A41D 20/00 2/16 |
| 5,474,524 A * | 12/1995 | Carey | A41D 13/065 602/14 |
| 5,642,525 A * | 7/1997 | Ketola | A41D 13/08 2/16 |
| 5,822,794 A | 10/1998 | Allred | |
| 6,092,235 A * | 7/2000 | Santa Cruz | A41D 13/08 2/93 |
| 6,158,051 A * | 12/2000 | Belzidsky | A41D 13/06 2/22 |
| 6,192,519 B1 * | 2/2001 | Coalter | A41D 13/088 2/16 |
| 6,405,381 B1 * | 6/2002 | Bowman, Jr. | A41D 27/08 2/161.1 |
| 6,472,590 B1 | 10/2002 | Kulik | |
| D774,280 S | 12/2016 | Hakeem | |
| 9,924,750 B2 | 3/2018 | MacNeil | |
| 10,159,779 B2 | 12/2018 | Olivarez | |
| 10,369,400 B2 | 8/2019 | Pozo | |
| 2001/0047531 A1 * | 12/2001 | Spies | A41D 13/08 2/22 |
| 2004/0187184 A1 | 9/2004 | Rubin et al. | |
| 2005/0028563 A1 * | 2/2005 | Mullins | A41D 31/30 66/202 |
| 2005/0112975 A1 * | 5/2005 | McMurray | D04B 21/18 442/306 |
| 2006/0042327 A1 * | 3/2006 | Hummel | D04B 1/24 66/202 |
| 2007/0028345 A1 | 2/2007 | McCarty | |
| 2009/0024065 A1 * | 1/2009 | Einarsson | A61B 5/486 600/587 |
| 2009/0049579 A1 | 2/2009 | Roberts | |
| 2010/0000005 A1 | 1/2010 | Dossman | |
| 2010/0024088 A1 | 2/2010 | Griefer | |
| 2010/0056973 A1 | 3/2010 | Farrow et al. | |
| 2010/0229278 A1 | 9/2010 | Bates | |
| 2010/0312160 A1 * | 12/2010 | Creighton | A61L 15/58 602/62 |
| 2012/0010551 A1 * | 1/2012 | Farrow | A61H 9/005 602/75 |
| 2012/0204319 A1 | 8/2012 | Gambordella | |
| 2012/0297517 A1 | 11/2012 | Abu-Bakr | |
| 2013/0042378 A1 | 2/2013 | Wu et al. | |
| 2013/0104275 A1 * | 5/2013 | Lea | A41D 13/08 2/16 |
| 2013/0254967 A1 | 10/2013 | Tiemann | |
| 2014/0223630 A1 | 8/2014 | Johnson | |
| 2014/0325729 A1 * | 11/2014 | Hsieh | A41D 13/08 2/24 |
| 2014/0359913 A1 * | 12/2014 | Magri | A41D 13/0543 2/22 |
| 2015/0196818 A1 | 7/2015 | Lein | |
| 2015/0264995 A1 * | 9/2015 | Hilderbrand, IV | A41B 11/008 2/455 |
| 2016/0017521 A1 * | 1/2016 | Thomson | D03D 1/0041 428/221 |
| 2016/0095371 A1 | 4/2016 | Beland et al. | |
| 2016/0332058 A1 | 11/2016 | Best et al. | |
| 2016/0353814 A1 * | 12/2016 | Hart | A41D 13/08 |
| 2017/0000196 A1 * | 1/2017 | Rivera | A41D 13/08 2/16 |
| 2017/0127740 A1 | 5/2017 | Bratskeir | |
| 2018/0084846 A1 * | 3/2018 | Rivera | A41D 13/08 |
| 2018/0098587 A1 | 4/2018 | Moore | |
| 2019/0350269 A1 * | 11/2019 | DeSimone | A41B 7/00 |
| 2020/0121002 A1 | 4/2020 | Schultz | |
| 2021/0360994 A1 * | 11/2021 | Takada | A41D 13/0525 |
| 2022/0370853 A1 * | 11/2022 | Henderson | A61B 5/6895 |

OTHER PUBLICATIONS

International Search Report issued in PCT/US20/47423 dated Nov. 4, 2020.

Wainwright, H.L., "Design, evaluation and application of electronic textiles" Performance Testing of Textiles, pp. 193-215 (2016) cited in ISR submitted herewith.

* cited by examiner

APPENDAGE GARMENT WITH ENHANCED TRACTION

CROSS-REFERENCE TO RELATED APPLICATIONS

The present application is a U.S. National Phase Application under 35 U.S.C. § 371 of International Patent Application No. PCT/US2020/047423 filed Aug. 21, 2020, which application claims priority to U.S. Provisional Application No. 62/890,109 titled "ENHANCED TRACTION, PROTECTIVE, AND COOLING ARM SLEEVE" filed Aug. 22, 2019, incorporated by reference herein as if set forth in its entirety.

BACKGROUND

Compression garments in sports are primarily geared toward optimal performance, protection, and recovery. Recent athletic wear designs have focused on the "5Ps model" to accomplish those goals, focusing on the physical, psychological, physiological, psychophysical and psychophysiological properties of garments. Previous studies have tested these measures using methods like maximal oxygen consumption (VO2 max) tests for physical performance, infrared cameras for thermoregulation values, and transdermal exudate samples in creatine kinase analysis for recovery. Currently, compression garments are designed primarily considering compression, sweat wicking, and skin protection. Fabric of compression garments typically includes fibers which blend materials including polyester, thermoplastic polyurethane elastomers ("spandex"), and nylon, which results in a fabric that slides relatively easy against skin and many other surfaces. Some compression garments include molded foam polystyrene padding to provide impact protection and/or thermal insulation.

SUMMARY

A multifunctional garment and methods related thereto are presented. When worn as a compression sleeve to play rugby, American football and other ball-carrying sports (with oblong or round balls), or when worn to carry objects during physical labor, an object contact surface positioned on the inner forearm of the sleeve can grip the carried object with increased friction while an outside facing surface of the sleeve can be smooth to deflect defenders or objects that may impact the sleeve, can be padded to protect from impacts, can provide protection from contusions and lacerations, and/or can provide active cooling. The object contact surface can also protect against abrasions and lacerations due to contact with objects or people likely to occur during various use cases such as those described herein. The garment can further include static or dynamic readable symbols or images woven or knitted into the garment (rather than printed or fused onto the garment).

An example garment can include a substantially tubular textile having an interior, an exterior, two open ends, a length extending from each of the open ends across the tubular textile, and a circumference circumscribing the tubular textile. The garment can have a first surface on the exterior of the tubular textile. The first surface can extend a majority of the length of the tubular textile and over a first portion of the circumference of the tubular textile. The garment can have a second surface on the exterior of the tubular textile. The second surface can extend a majority of the length of the tubular textile and over a second portion of the circumference of the tubular textile. The first surface can have a greater coefficient of friction compared to the second surface, where the term "coefficient of friction" is understood as defined herein. The example tubular textile can be sized, shaped, and otherwise configured to be worn over an arm, leg, mid-section, or other body part. When configured to wear over a leg, the garment can be invertible such that the first and second surfaces are configured to be worn against skin of the leg.

Another example garment can include a sleeve having an exterior, an interior, and a circumference. The sleeve can be configured with two open ends, as in the above described example garment, or can be integral to a shirt, bodysuit, or other article of clothing. The sleeve can include an exterior, an interior, and a circumference. The sleeve can have a first surface on the exterior that extends over a first portion of the circumference of the sleeve. The sleeve can have a second surface on the exterior that extends over a second portion of the circumference, opposite the first surface. The first surface can have a greater coefficient of friction compared to the second surface, where the term "coefficient of friction" is understood as defined herein.

Either of the aforementioned example garments can be sized to fit over a forearm and elbow of a human.

Either of the aforementioned example garments can include a third surface on the interior of the tubular textile or the sleeve. The third surface can extend under a majority of the first and/or second surface. The third surface can have a coefficient of friction less than the coefficient of friction of the first surface. Either of the aforementioned example garments can include a warp knit fabric forming the first surface on the exterior of the garment and the third surface on the interior of the garment. The warp knit pattern of the fabric can cause the third surface to have a coefficient of friction less than the coefficient of friction of the first surface. The first, second, or third surface can include a pocket for a pulse rate, blood oxygen level, or other health sensing device. Additionally, or alternatively, the garment can include an inner liner extending under the first and/or second surface that is of a separate layer under fabric of the first and/or second surface.

Either of the aforementioned example garments can include at least one of polyurethane, polyamide, polypropylene, polyester, and silicone elastomer.

For either of the aforementioned example garments, the first surface can include a 3-D textured knitted surface having a greater coefficient of friction compared to the second surface. The 3-D textured knitted surface can include knitted patterns of readable symbols.

For either of the aforementioned example garments, the first surface can include an active display. The active display can include remotely or locally programmable pixels. For either of the aforementioned example garments, the first surface can include light emitting fibers.

For either of the aforementioned example garments, the second surface can include an active display. The second surface can include remotely or locally programmable pixels.

For either of the aforementioned example garments, the second surface can include light emitting fibers.

Either of the aforementioned example garments can include a seamless transition between the first surface and the second surface. Additionally, or alternatively, either of the aforementioned example garments can include a seam joining the first surface to the second surface, the seam formed by stitching, adhesive glues, ultrasonic weld and/or thermal weld.

Either of the aforementioned example garments can include a thickened region positioned under the second surface comprising a thickness greater than a majority of fabric of the garment. The thickened region can include foam.

Either of the aforementioned example garments can include a pocket positioned under the second surface and sized to receive padding. For either of the aforementioned example garments, the first, second or third surface can include fibers that are able to sense and detect pulse rate, blood oxygen level, pH, or other health sensing metrics.

Either of the aforementioned example garments can include a first silicone band affixed to the interior and positioned to be worn approximate to a wrist and a second silicone band affixed to the interior and positioned to be worn over a bicep.

Either of the aforementioned example garments can include a fabric spanning across the second surface. The fabric can have a surface smoothness on the interior effective to promote donning and doffing the garment, augmented thermal transport, moisture wicking properties, antimicrobial, antiviral, and/or odor control properties.

For either of the aforementioned example garments, the first surface against a leather or polymeric ball can have a static coefficient of friction and/or kinetic coefficient of friction sufficient to inhibit the leather or polymeric ball from disengaging the first surface when the first surface is positioned on a forearm of an athlete and the athlete is carrying the leather or polymeric ball via compression to the first surface. The leather or polymeric ball can be round or oblong.

For either of the aforementioned example garments, the first surface against each of a wood surface, a metal surface, and a cardboard surface of respective objects can have a static coefficient of friction and/or kinetic coefficient of friction sufficient to inhibit the respective objects from disengaging the first surface when the first surface is positioned on a forearm of a human wearer is carrying the respective objects via compression to the first surface.

Either of the aforementioned example garments can be effective to protect from contusions and lacerations, provide active cooling, and/or provide compression to increase strength, reduce muscle fatigue and promote healing.

Either of the aforementioned example garments can be abrasion and cut resistant.

For either of the aforementioned example garments, when the garment is worn on an arm, the first surface can include a knitted periodic pattern such as a honeycomb pattern. The knitted periodic pattern can be effective to transfer energy from an impact to the pattern. Additionally, or alternatively, the first surface can include a knitted random pattern. The knitted random pattern can be effective to transfer energy from an impact to the pattern.

For either of the aforementioned example garments, when the garment is worn on an arm, the second surface comprises smoothness effective to inhibit an opposing player from grabbing the garment and/or mitigating glancing impacts.

For either of the aforementioned example garments, when the garment is worn on an arm, the second surface further includes a knitted honeycomb or other pattern. The knitted honeycomb and/or other pattern can be effective to transfer energy from an impact to the pattern.

For either of the aforementioned example garments, the first and/or second surface can further include durable customized school or team names and/or logos, text and/or numbers via selectively knitted and/or dyed thread.

For either of the aforementioned example garments, the first surface can have a greater coefficient of friction when wet compared to the first surface when dry. The second surface can have a lower coefficient of friction when wet compared to the second surface when dry.

An example method can include some or all of the following steps performed in various order and additional steps as understood by a person skilled in the pertinent art. A sleeve can be positioned on an arm such that an object contact surface of the sleeve is positioned on an inner forearm of the arm and an outside facing surface of the sleeve is positioned on an outer forearm of the arm. An object can be carried via compression of the object to the first surface, the object contact surface.

The example method can further include wearing the sleeve while carrying a ball, the ball being the carried object. The example method can further include carrying the ball via compression of a leather or polymeric surface of the ball to the object contact surface and compression of the ball to a torso.

The example method can further include wearing the sleeve while playing one of American football, rugby, soccer, or volleyball.

The example method can further include shedding a defender attempting to grab the outside facing surface or wearer.

The example method can further include utilizing fabric of the outside facing surface to absorb impacts to the outside facing surface.

The example method can further include wearing the sleeve while carrying a cardboard box, paper box, or wooden box, the box being the carried object. The example method can further include carrying the box via compression of the box to the object contact surface. The example method can further include wearing a second sleeve on the opposing arm, the second sleeve being substantially similar to the aforementioned sleeve and worn similarly as the aforementioned sleeve. The example method can further include carrying the box via compression of the box between respective object contact surfaces of the two sleeves.

The carried object can be one of a home appliance, a garbage bag, and a plastic container. The example method can further include carrying the object via compression of a leather, wood, metal, plastic, paper, and/or cardboard surface of the object to the object contact surface.

The example method can further include carrying the object as part of a construction working task. The example method can further include carrying the object as part of a yard working task. The example method can further include carrying the object as part of farm work. The example method can further include carrying the object as part of warehouse, delivery, package, and baggage handling work. The example method can further include carrying the object as part of a manufacturing or mill work task. The example method can further include wearing the sleeve while acting as a baseball or softball catcher blocking a pitch. The example method can further include wearing the sleeve while climbing objects as in lumberjacking, rock climbing, bouldering, orienteering, and by utility linemen. The example method can further include wearing the sleeve while grasping humans in wrestling, rugby, American Football, or other sport that relies on contact with an opposing human. The example method can further include wearing the sleeve while catching and throwing humans as with cheerleading teammates and dancing partners. The example method can further include wearing the sleeve while grasping humans in wrestling, rugby, American Football, or other sport that relies on contact with an opposing human. The example method can further include wearing the sleeve while playing water polo, swimming, diving, or SCUBA diving. The example method can further include wearing the sleeve while fishing, the object being a fish and engaging the fish via friction to the object contact surface.

The example method can further include using light emitting fibers of the sleeve to create synchronized gestures and patterns among groups of humans.

The example method can further include reading symbols displayed on the object contact surface.

Another example method can include some or all of the following steps performed in various order and additional steps as understood by a person skilled in the pertinent art. A tubular garment can be worn. The tubular garment can include an interior, an exterior, two open ends, and a length extending between the two open ends. The tubular garment can be secured in place over a lower leg at least in part due to a static and/or kinetic coefficient of friction between skin of the lower leg and a first surface on the interior of the garment, the first surface extending over a majority of the length of the garment, the static coefficient of friction and the kinetic coefficient of friction between skin and the first surface being greater than static coefficient of friction and kinetic coefficient of friction between skin and a second surface on the interior of the garment and extending over a majority of the length of the garment. The garment can be doffed by pulling the first surface away from the skin of the lower leg and pulling the second surface against the skin of the lower leg.

Another example method can include wearing any of the example garments presented herein and using said garment in a medical application.

DETAILED DESCRIPTION

Figure 1:
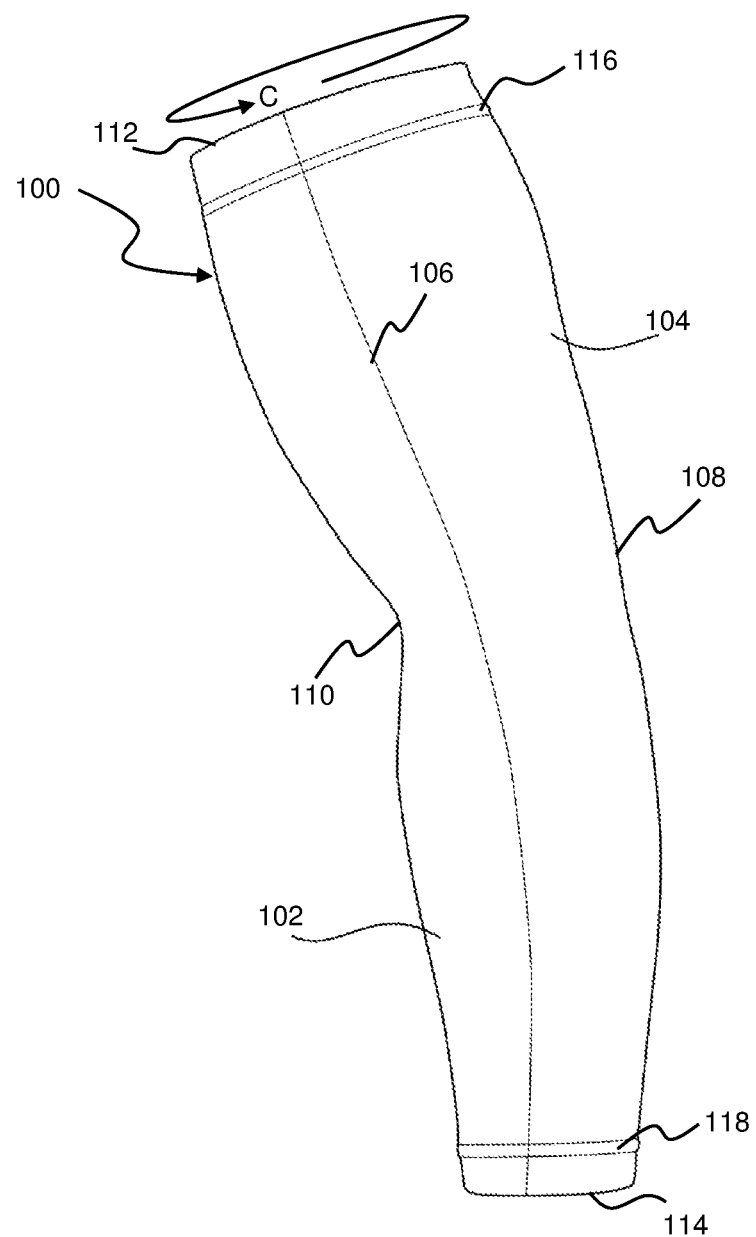
FIG. 1 is an illustration of an example garment according to aspects of the present invention.

As used herein, the term "coefficient of friction" is a comparative property of a surface when compared to a "coefficient of friction" of another surface. A first surface having a higher or lower coefficient of friction as compared to a coefficient of friction of a second surface is understood to mean that a static coefficient of frication $\mu_s$ and a kinetic coefficient of friction $\mu_k$ between the first surface and skin or a majority of other common reference surfaces are each respectively higher or lower than a static coefficient of friction $\mu_s$ and a kinetic coefficient $\mu_k$ between the second surface and skin or the majority of other common reference surfaces. A surface with a lower coefficient of friction can have a smoother tactile feel and/or slide more easily over common reference surfaces compared to a surface with a higher coefficient of friction. A surface can be substantially flat or can have raised features positioned to affect the smoothness and coefficient of friction of the surface. As used herein, "static coefficient of friction", "$\mu_s$", "kinetic coefficient of friction", and "$\mu_k$" have their plain and ordinary meaning as understood by a person skilled in the pertinent art as understood according to the teachings herein.

As used herein, the terms "tubular" and "tube" are to be construed broadly and are not limited to a structure that is a right cylinder or strictly circumferential in cross-section or of a uniform cross-section throughout its length. A tubular structure can have a linear, tapered or curved outer surface without departing from the scope of the present invention. As used herein, the term "circumference" in reference to a tube or tubular shape is in relation to a direction which circumscribes the tubular shape about an axis of the tubular shape. The circumference can vary in dimension along a tube unless specified otherwise.

Example garments illustrated and otherwise disclosed herein can function as a multifunctional piece of athletic wear. When worn as a sleeve to play rugby, American football and other ball-carrying sports (with oblong or round balls), the sleeve may provide increased ball security, protection from contusions and lacerations, active cooling, and/or compression to increase strength, reduce muscle fatigue and promote healing as a non-limiting list.

Example garments can include a textile tube with an interior surface (skin facing) that, when in contact with skin results in a sufficiently low static coefficient of friction and sufficiently low kinetic coefficient of friction to promote donning and doffing the garment. Other properties of the skin-facing surface can include augmented thermal transport, moisture wicking, antimicrobial, antiviral, and odor control.

When worn as a sleeve, the garment includes two surfaces each over about half of the garment's circumference: an object contact surface and an outside facing surface, where the object contact surface is positioned inside the forearm (and potentially bicep) to press into the football when carried and the outside facing surface is positioned outside the forearm (and potentially bicep) to face a defender or tackler. The fabric of the object contact surface can include fiber material content and/or be woven and/or knitted in such a way as to provide a high static coefficient of friction and/or kinetic coefficient of friction between the object contact surface and the ball to promote ball security. In some examples, the static coefficient of friction and/or kinetic coefficient of friction between the object contact surface and the ball can be increased when the object contact surface becomes wet.

Knitted patterns can be 3D textured on the object contact surface. The static patterns can be random, periodic, and/or include symbols or letters/number to also provide information (plays, words, logos). The patterns, whether visibly raised or not, can provide a sufficiently high static and/or kinetic coefficient of friction between the ball and the object contact surface to improve ball security. Additionally, or alternatively, active displays can be knitted or woven within the sleeve as 'pixels' for transient information display. For instance, the object contact surface can include optical, light emitting fibers to provide remotely or locally programmable pixels. The light emitting from the pixels may be of visible, infrared, or ultraviolet wavelengths. The information displayed on the programmable pixels may be controlled directly by wearer input or remotely by radio frequency (Bluetooth®, Wi-Fi, 5G, UHF, VHF, etc.). The object contact surface can therefore provide a dual function by providing a high coefficient of friction to help prevent fumbles, as well as information and communication to promote correct alignment and play among teammates and remote coaching staff.

Contrastingly, the outside facing surface, when in contact with skin, can result in a much lower static and/or kinetic coefficient of friction compared to the object contact surface and skin so that the outside facing surface is more difficult to grip by an opposing players compared to the object contact surface. Glancing hits to the arm can be mitigated by the smoothness of the outside facing surface. Information (logos, patterns, text, etc.) can be knitted and/or woven into the outside facing surface to present visual imagery either in the traditional 'static' sense, or as active 'pixel-based' displays. The information can be knitted and/or woven in a jacquard fabric, where the information is incorporated into the knit or weave of the fabric rather than being printed or dyed onto the surface of the fabric. The outside facing surface can include augmented thermal transport, moisture wicking, antimicrobial, antiviral, and odor control. In some examples, the static coefficient of friction and/or kinetic coefficient of friction between the outside facing surface and skin or other reference object can be reduced when the outside facing surface becomes wet.

Knitted patterns can be 3D textured on the outside facing surface. The static patterns can be random, periodic, and/or include symbols or letters/number to also provide information (plays, words, logos). Additionally, or alternatively, active displays can be knitted or woven within the sleeve as 'pixels' for transient information display. For instance, the outside facing surface can include optical, light emitting fibers to provide remotely or locally programmable pixels. The light emitting from the pixels may be of visible, infrared or ultraviolet wavelengths. The information displayed on the programmable pixels may be controlled directly by wearer input or remotely by radio frequency (Bluetooth®, Wi-Fi, 5G, UHF, VHF, etc.). The outside facing surface can therefore provide a dual function by providing a low coefficient of friction to help promote defender shedding, as well as information and communication to promote correct alignment and play among teammates and remote coaching staff.

Material on the inside of the bicep and wrist cuffs can be included to ensure a secure and comfortable fit. For instance, silicone or elastic strips can be included on inside of cuffs to provide a friction fit to skin. Cuffs can be made with additional layers of material to add cushion for impact and/or increase force required to stretch the cuffs. Cuffs can be adjustable in size e.g., with an adjustable elastic band, hook and loop closure, or other such means to provide adjustable fit in clothing. The garment can include fibers to detect human health condition (pulse, respiration rate, O2 levels, pH, etc.). The garment can include a pocket for a pulse rate, blood oxygen level, or other health tracking device in a location not likely to impede physical activity while wearing, e.g. on bicep near an armpit or on outside of wrist.

The garment can include a honeycomb patterned (or other suitable pattern) 3-D 'padding' on the outside facing surface to reduce the energy transfer of a hit. The honeycomb can be a jacquard pattern knitted or woven into fabric of the outside facing surface. The garment can include durable customized school or team logos, letters, numbers or other symbols via selectively knitting or weaving dyed thread (i.e., not screen-printed with ink). The garment can include materials (fibers, coatings, other functionalization, etc.) to asymmetrically alter the coefficient of friction of the sleeve (i.e., if wet, it decreases coefficient of friction, on outside surface, but provides greater coefficient of friction to the ball on the object contact surface).

The garment can include customization of textile composition/texture at differing locations on the sleeve, based on individual preference. The garment can have an elastic property to create a secure and comfortable fit. The garment can be produced in different sizes ranging from child to adult. As a sleeve, the garment can be fabricated with different styles, including but not limited to, forearm, ¾, full arm, and clothing integration.

The garment can be treated with an anti-microbial such as a zinc, silver, copper, or chlorhexidine gluconate either entirely or in selective locations.

Some advantages over present technologies can include arm sleeve multifunctionality. When worn as a sleeve, the garment can be configured to offer athletes increased ball security, increased protection, cooling, compression, alignment cues, the option for customization to include logos and/or alphanumeric characters, as well as communication abilities, or any combination thereof.

The garment may also be worn advantageously in other contexts where the wearer can make use of contact friction between the object contact surface and any number of surfaces including skin, leather, wood, plastic, metal, cardboard, paper, vegetative debris, other textiles, fish scales, etc. and the smoother outside facing surface. For instance, the garment can be worn as a sleeve to carry objects moving boxes, performing construction work, performing farm work, performing yard work, performing warehousing delivery, moving appliances, catching large fish, etc. In some examples, it can be advantageous to wear the object contact surface against the skin to prevent the garment from moving out of place, and the smoother outside facing surface can be positioned against skin to facilitate donning and doffing of the garment by providing a smooth surface opposite the object contact surface against which skin can easily slide.

The garment can be abrasion or cut resistant. The garment can be effective to protect from contusions and lacerations. The garment can be effective to provide active cooling. The garment can be effective to provide compression to increase strength, reduce muscle fatigue and promote healing.

The garment can be effective to promote medical recovery and healing through the emission of visible, ultraviolet and infrared wavelengths of light.

Figure 2A:
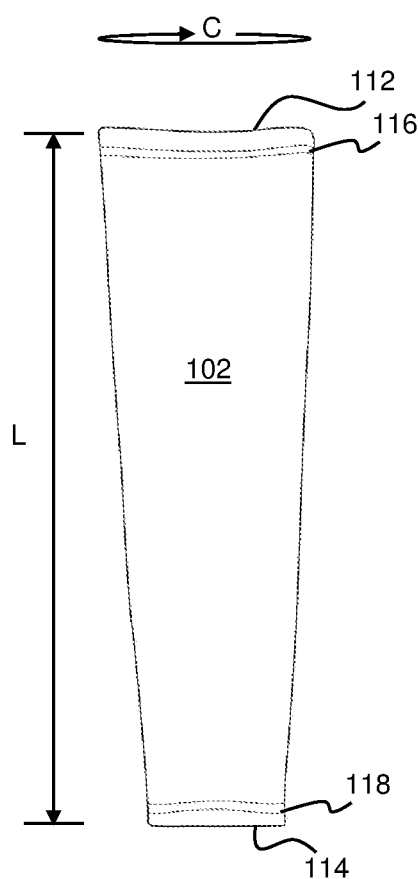
FIGS. 2A and 2B are additional views of the garment illustrated in FIG. 1.
Figure 2B:
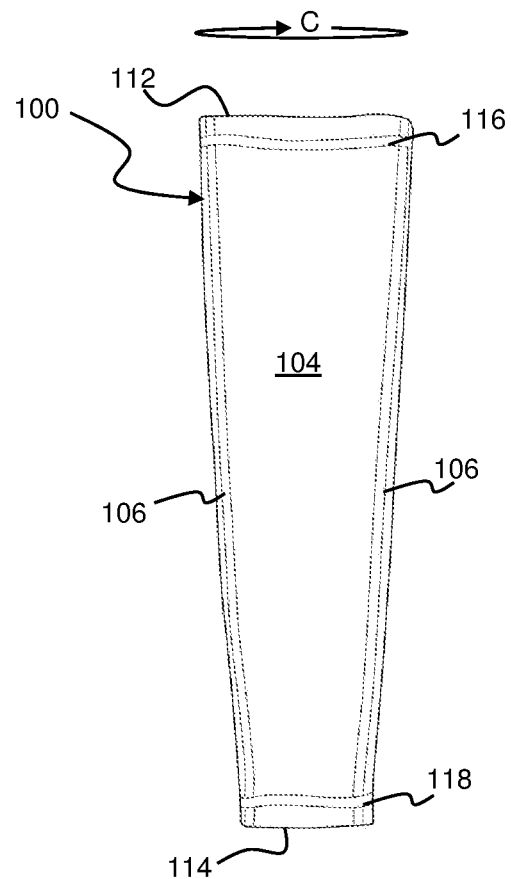

FIG. 1 is an illustration of an example garment 100 in a shape as worn as a sleeve over and arm. FIGS. 2A and 2B are illustrations of opposite sides the garment 100 lying flat in a relaxed shape. The garment 100 can include any of the aforementioned features, benefits, and functionality. Aforementioned features not specifically illustrated can be incorporated into the garment 100 as understood by a person skilled in the pertinent art according to the teachings herein.

Referring collectively to FIGS. 1 through 2B, the garment 100 can have a tubular shape with a larger open end 112 sized to fit over a bicep and a smaller open end 114 sized to fit around a wrist. The outside of the tubular garment 100 can have two surfaces 102, 104 having differing surface properties to result in differing frictional forces when applied to a given surface such as skin, leather, cardboard, wood, plastic, metal, etc. One of the two surfaces 102, 104 can be an object contact surface 102 that has surface properties to cause engagement by friction of the object contact surface 102 to a surface of an object that is carried by a wearer of the garment 100. The garment 100 can be worn so that the object contact surface 102 faces upwardly and/or toward the wearer's body, on the inside 110 of the elbow. The other of the two surfaces 104 can be an outside facing surface 104 that can be positioned on an opposite of the tubular shape from the contact surface 102, facing away from the wearer's body, on the outside 108 of the elbow. The outside facing surface 104 can have surface properties that are less likely to cause engagement by friction to a surface of a given object compared to the object contact surface 102. Preferably, the object contact surface 102 has a higher coefficient of friction than the other, outside facing surface 104, where "coefficient of friction" is contextually used as a comparative property of a surface as defined hereinabove. The outside facing surface 104 can be designed to have desirable material properties such as cooling, object deflection, impact protection, moisture wicking, antimicrobial, antiviral, odor control, display symbols such as text, numbers, logo, etc. The object contacting surface 102 can be designed to have desirable material properties such as cooling, impact protection, moisture wicking, antimicrobial, antiviral, odor control, display symbols such as text, numbers, logo, etc.

The object contact surface 102 can enable the wearer to maintain possession of an object carried against the object contact surface 102. The garment 100 can be worn as a sleeve by a user engaged in physical labor to help the wearer's arms to engage and carry boxes, bags, equipment, tools, appliances, etc. The garment 100 can be worn as a sleeve during a ball carrying sport such as (but not limited to) rugby or American football to help a ball carrier to secure the ball. For ball carrying sports, the outside facing surface 104 can be smooth to inhibit an opposing player from grabbing the sleeve and/or mitigate effects of glancing hits.

As an alternative, the example garment 100 can be configured to be worn inside out to as illustrated in FIG. 1. In which case, the higher friction object contact surface 102 can be configured to grip skin and maintain position of the garment 100 when worn during a physical activity, and the opposite surface 104 can be smoother than the object contact surface 102 to aid in donning and doffing the garment 100. As another alternative, the example garment 100 can be a shirt, pants, shin guard, socks, or other such garment. For instance, when worn inside out compared to as illustrated in FIG. 1 and worn as a shin guard over a lower leg, friction between the object contact surface 102 and skin of the leg can prevent the shin guard from changing position, slipping or falling down when the wearer is running, walking, jumping, hiking, orienteering, etc. The outside facing surface 104 can be sufficiently smooth so that the wearer can pull the outside facing surface 104 into skin of the leg and the object contact surface 102 away from skin of the leg to don and doff the shin guard.

The garment 100 can be a compression garment that, when worn, is stretched circumferentially (C) and provides a compression force to the portion of the wearer's body under the garment 100. Configured as such, the garment 100 can have physical, psychological, physiological, psychophysical, and/or psychophysiological benefits of a compression garment. For instance, the garment 100 can provide protection from contusions and lacerations, provide active cooling, and/or reduce muscle fatigue.

The garment 100 can be constructed to have several geometries and constructed by several methods as understood by a person skilled in the pertinent art. The garment 100 as illustrated includes seams 106 joining two fabrics respectively spanning the two surfaces 102, 104. The seams 106 can be made flat similar to seams of contemporary compression garments via sewing, fusing, adhesive gluing, ultrasonic welding, and/or thermal welding. Alternatively, the two fabrics of the two surfaces 102, 104 can be joined seamlessly through seamless knitting or weaving techniques.

The garment 100 can include surfaces with sufficiently high friction against skin on the interior, skin facing, surface of the tube to prevent the garment 100 from undesirably slipping out of position on the wearer's body. For instance, the garment 100 can include bands of elastic or silicone rubber material near each opening 112, 114 on the interior surface of the tube to resist slippage of the garment 100 against the wearer's skin when worn. Alternatively, the garment 100 need not include such high friction surfaces as the underside of the fabric of the object contact surface 102 and/or outside facing surface 104 can provide sufficient friction against skin to resist slippage of the garment 100 against the wearer's skin when worn.

The garment 100 can be constructed to have two open ends 112, 114, thereby forming a tubular shape. The tubular garment 100 can include skin-facing silicone or elastic bands at positions 116, 118 near one or both of the open ends 112, 114 to prevent shifting of the garment 100 while being worn and performing various physical activities including activities described herein. Alternatively, although not illustrated as such, the garment 100 can be incorporated into a larger article of clothing such as a shirt, jacket, shrug, body suit, glove, etc. and extend from either of the illustrated open ends 112, 114 to the larger article of clothing. In addition, or as alternative to the silicone bands, the garment 100 can include other structures at similar positions 116, 118 or elsewhere to prevent shifting of the garment 100 such as stretch stitching, increased material thickness, stretch hem knit/weave structures, etc. In some examples, dimensions of the circumference (C) of the garment 100 at one or both of the open ends 112, 114 can be adjustable in size e.g. with an adjustable elastic band, hook and loop closure, or other such means to provide adjustable fit in clothing.

The garment 100 can include fibers at positions 116, 118 near the open ends 112, 114 or elsewhere to sense and detect human health condition (pulse rate, respiration rate, blood oxygen levels, pH, moisture level, etc.).

The garment 100 can be constructed to have a pocket for a pulse rate, blood oxygen level, or other health tracking device in a location not likely to impede physical activity while wearing, e.g. on bicep near an armpit or on outside of wrist.

Figure 3:
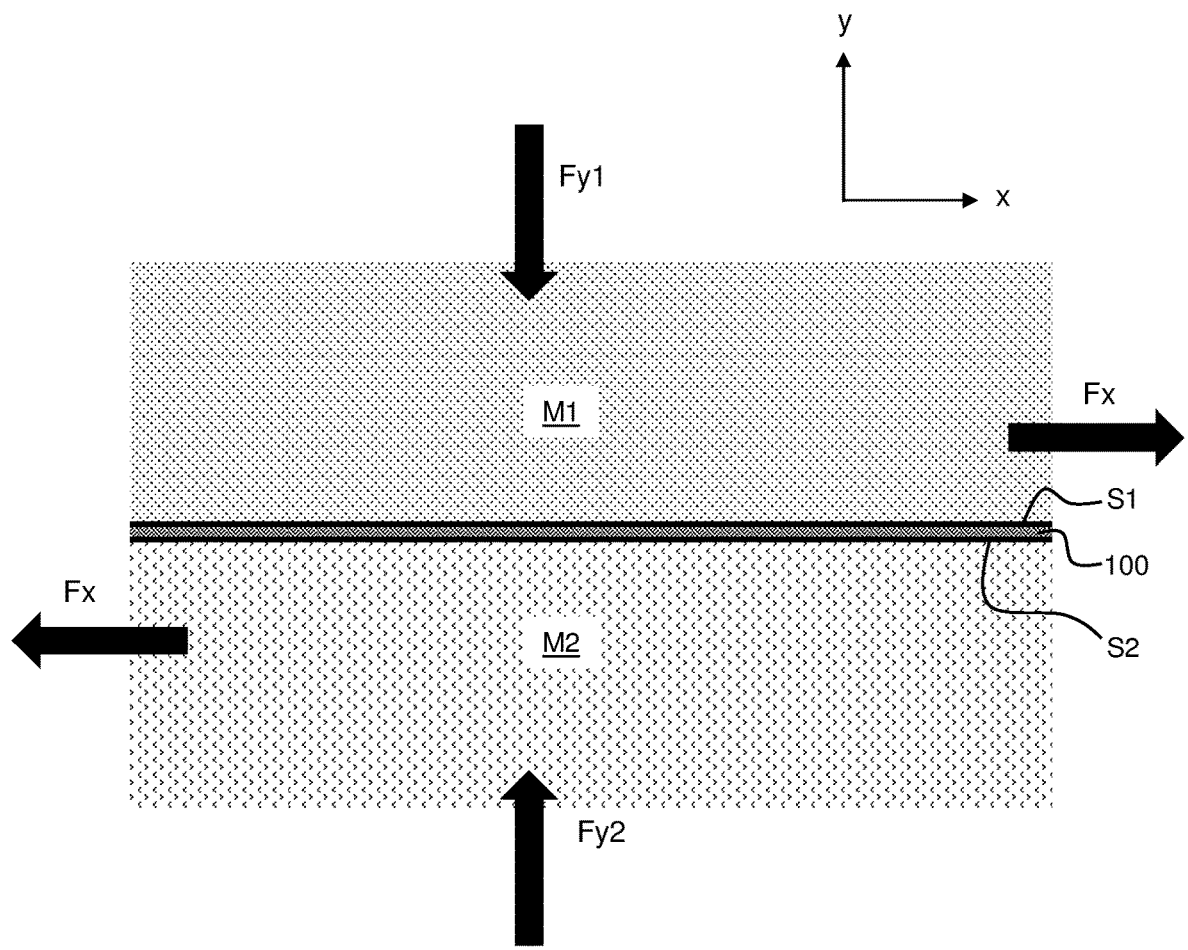
FIG. 3 is a free body diagram of the garment and applied forces which can result in frictional forces at garment surfaces according to aspects of the present invention.

FIG. 3 is a free body diagram illustrating forces Fx, Fy1, Fy2 applied to surfaces S1, S2 the garment 100 when the garment 100 is rubbed and compressed between two masses M1, M2. The lower mass M2 can represent a body part having skin that presses against an interior surface S2 of the garment 100 with an upwardly directed normal force Fy2 when the garment 100 is worn. The upper mass M1 can represent an object pressed to an exterior surface S1 of the garment 100 with a downwardly directed normal force Fy1. In some instances, the upwardly directed force Fy2 from the lower mass M2 can be about equal to the downwardly directed normal force Fy1 from the upper mass M1. When the garment 100 provides significant compression, the compression can additionally contribute to the normal force Fy2 between the garment 100 and skin (of the lower mass M2 as illustrated). In other words, when compression is significant, normal force Fy2 to the interior surface S2 of the garment 100 can be greater than the normal force Fy1 applied to the exterior surface S1 of the garment 100. The normal force Fy2 between the garment 100 and skin can also be manipulated when the garment is moved during donning, doffing, or adjusting. When either mass M1, M2 is moved against its associated surface S1, S2 of the garment 100, oppositely directed parallel forces Fx of equal magnitude are applied to the respective surfaces S1, S2, assuming each surface S1, S2 is in contact with the respective mass M1, M2.

Static friction between a respective mass M1, M2 and a respective surface S1, S2 can prevent movement of a mass M1, M2 in relation to its respective surface S1, S2 when the respective mass M1, M2 is stationary in relation to its respective surface S1, S2. Static friction between two surfaces can be quantified by a static coefficient of friction $\mu_s$. Kinetic friction between a respective mass M1, M2 and a respective surface S1, S2 can impede movement of the respective mass M1, M2 across its respective surface S1, S2 when the respective mass M1, M2 is in motion across its respective surface S1, S2. Kinetic friction between two surfaces can be quantified by a kinetic coefficient of friction $\mu_k$. Coefficients of friction $\mu_s$, $\mu_k$ can be calculated by methods known to a person skilled in the pertinent art.

In some examples, properties of the interior surface S2 can be designed to provide a desired static coefficient of friction $\mu_s$ and/or kinetic coefficient of friction $\mu_k$ between the interior surface S2 and skin of a body (M2 as illustrated). Increasing the static coefficient of friction $\mu_s$ and/or kinetic coefficient of friction $\mu_k$ between the interior surface S2 and skin can help keep a garment in place when worn. Decreasing the static coefficient of friction $\mu_s$ and/or kinetic coefficient of friction $\mu_k$ between the interior surface S2 and skin can increase ease of a user to don and doff the garment 100. While wearing, and when donning and doffing the garment 100, compression can be a significant factor which determines the normal force Fy2 of skin against the interior surface S2. Pressing an object to the exterior surface S1 of the garment 100 can also contribute to the normal force Fy2 of skin against the interior surface S2. When donning and doffing the garment, the static coefficient of friction $\mu_s$ and/or kinetic coefficient of friction $\mu_k$ between the interior surface S2 and skin is preferably low enough so that the wearer can readily apply a parallel force Fx that overcomes frictional force resulting from the normal force Fy2 between skin and the interior surface S2. When the garment 100 is worn, the static coefficient of friction $\mu_s$ and/or kinetic coefficient of friction $\mu_k$ between the interior surface S2 and skin is preferably high enough to cause a frictional force resulting from the normal force Fy2 that is sufficient to resist expected parallel force Fx that may occur during intended use of the garment 100.

In some examples, properties of the exterior surface S1 can be designed to provide a desired static coefficient of friction $\mu_s$ and/or kinetic coefficient of friction $\mu_k$ between the exterior surface S1 and surface of an object (M1 as illustrated). Increasing the static coefficient of friction $\mu_s$ and/or kinetic coefficient of friction $\mu_k$ between the exterior surface S1 and the surface of the object M1 can facilitate engagement between the object M1 and the garment 100. Decreasing the static coefficient of friction $\mu_s$ and/or kinetic coefficient of friction $\mu_k$ between the exterior surface S1 and the object M1 can increase ease of a user to deflect or disengage the object M1. Pressing the object to the exterior surface S1 of the garment 100 primarily contributes to the normal force Fy1 of the object against the exterior surface S1. The normal force Fy1 and parallel force Fx that may occur during intended use of the garment 100, and the intent of the exterior surface S1 for engagement or deflection are considerations that be used to determine desired static coefficient of friction $\mu_s$ and/or kinetic coefficient of friction $\mu_k$ between the exterior surface S1 and surface of the object M1.

Coefficient of friction $\mu_s$ and kinetic coefficient of friction $\mu_k$ between the exterior surface S1 and the object M1 are each dependent on surface properties of both the exterior surface S1 and the surface of the object M1, meaning contact of the exterior surface S1 to one object causes a different $\mu_s$ and $\mu_k$ compared to contact of the exterior surface S1 to a different object. For instance, $\mu_s$ and $\mu_k$ between the exterior surface S2 of the garment and leather can be different than $\mu_s$ and $\mu_k$ between the exterior surface S2 and cardboard, skin, plastic, wood, or metal, etc. Surface properties of objects expected to come into contact with the exterior surface S2 is therefore also a consideration that can be used to determine desired static coefficient of friction $\mu_s$ and/or kinetic coefficient of friction $\mu_k$ between the exterior surface S1 and surface of the object M1.

Referring again to FIGS. 1 through 2B, the relative smoothness of the object contact surface 102 compared to the outside facing surface 104 can be quantified based on static coefficient of friction $\mu_s$ and/or kinetic coefficient of friction $\mu_k$ between those surfaces 102, 104 and a given reference surface, where the smoother surface has lower $\mu_s$ and/or pk. In textiles, skin is often used as such a reference surface to quantify a touch quality of fabric. For use cases of the garment involving carrying of objects, a material of an object that might be carried in an intended use case can be used as the reference surface. For instance, wood, metal, leather, plastic, paper, cardboard, etc. can be used as the reference surface.

Although $\mu_s$ and $\mu_k$ may vary depending on the reference surface, it is likely that if the object contact surface 102 is found to have a higher $\mu_s$ and/or $\mu_k$ for a given reference surface (compared to $\mu_s$ and/or $\mu_k$ between the outside facing surface 104 and the same reference surface), then the object contact surface 102 will also have a comparatively higher $\mu_s$ and/or $\mu_k$ against additional reference surfaces (compared $\mu_s$ and/or $\mu_k$ between the outside facing surface 104 and the each respective additional reference surface). Further, although it is possible for one surface in contact to a reference surface to have a higher $\mu_s$ and lower $\mu_k$ (or vice versa) compared to another surface in contact with the reference surface, when a significant difference in smoothness between the two surfaces exists, both $\mu_s$ and $\mu_k$ are higher for one surface and lower for the other. To that end, although neither $\mu_s$ nor $\mu_k$ are inherent properties of a given material, for ease of discussion, and as used herein, a surface is described as having a higher (or lower) "coefficient of friction" than another surface when both $\mu_s$ and $\mu_k$ are higher (or lower) when the former aforementioned surface is pressed to skin or a majority of other common reference surfaces compared to when the latter surface is pressed to skin or the majority of other common reference surfaces.

Referring again to the garment 100 illustrated in FIGS. 1 through 2B, the object contact surface 102 can have a higher coefficient of friction compared to the outside facing surface 104. Although a crude test, difference in coefficient of friction between the object contact surface 102 and the outside facing surface 104 can be observed by sliding a finger against each surface 102, 104, maintaining approximately constant pressure and speed, and observing greater resistance to the sliding finger on the object contact surface 102 compared to the outside facing surface 104.

The object contact surface 102 can have a substantially uniform smoothness over a majority of its surface area. The outside facing surface 104 can have a substantially uniform smoothness over a majority of its surface area. Configured as such, the majority of the surface area of the object contact surface 102 can have a coefficient of friction that is greater than a coefficient of friction of the majority of the surface area of the outside facing surface 104. When the garment 100 is worn as a sleeve as illustrated in FIG. 1, the object contact surface 102 extends from the wearer's wrist (at the wrist opening 114) to bicep (at the bicep opening 112) on approximately half of the circumference (C) of the sleeve 100. The outside facing surface 104 extends the remainder of the circumference (C) of the sleeve 100. In some applications, the object contact surface 102 can extend only between the wrist and elbow 110 as the interior of the forearm is more likely than the bicep to engage objects when the wearer is carrying objects. The sleeve can be cut short so that it extends only to the elbow, or the bicep portion of the sleeve can include fabric of the outward facing surface 104 around the entire circumference of the bicep.

Figures 4A, 4B:
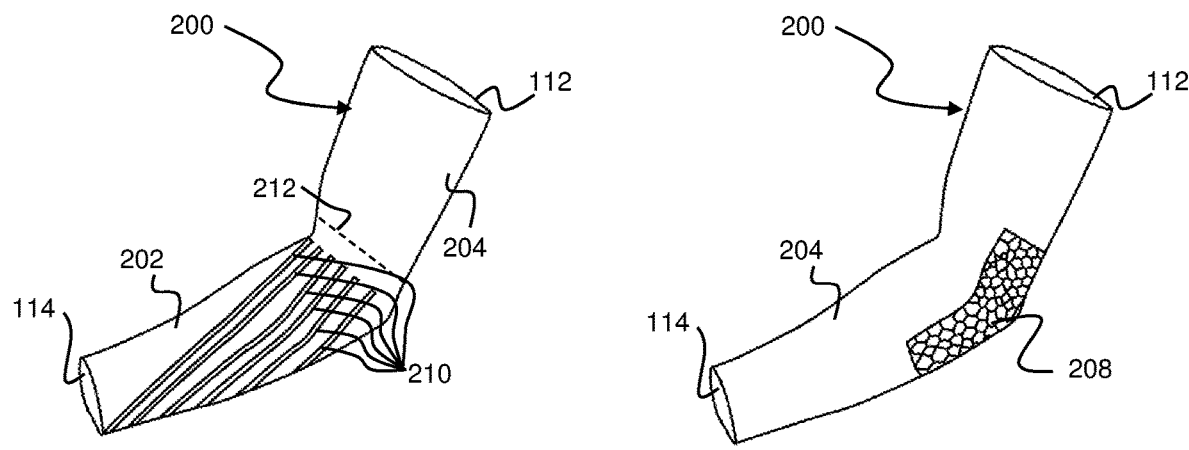
FIGS. 4A through 4C are an illustrations of another example garment according to aspects of the present invention.
Figure 4C:
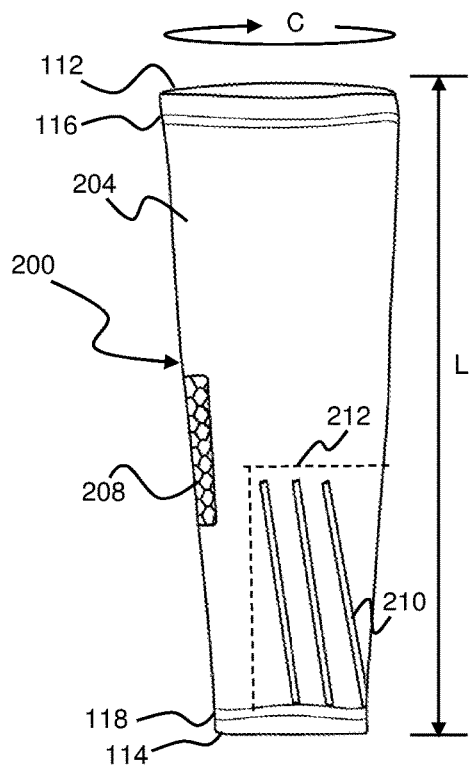

FIGS. 4A through 4C is an illustration of another example garment 200. The garment 200 can be worn as a sleeve as illustrated in FIGS. 4A and 4B. The garment 200 is illustrated in a flat, relaxed shape in FIG. 4C. The garment 200 as illustrated includes a tubular outer surface that has substantially uniform smoothness with the exception of raised strips 210 of comparatively higher coefficient of friction and an elbow pad 208. The strips 210 are positioned on the inside of the wearer's forearm to define an object contact surface 202. A dashed line 212 is drawn in FIGS. 4A and 4C is illustrated to roughly demark a boundary between the object contact surface 202 and a remainder 204 of the exterior surface of the garment 200. The remainder 204 includes a portion of the garment 200 surrounding the bicep and a portion of the garment 200 worn on the outside of the forearm.

Features of the garment 200 illustrated in FIGS. 4A through 4C can be combined with features of the garment 100 illustrated in FIGS. 1, 2A, and 2B. For instance, elbow padding 208 and/or strips 210 of the garment 200 illustrated in FIGS. 4A through 4C can be added to the garment 100 illustrated in FIGS. 1, 2A, and 2B. Likewise, the garment 200 illustrated in FIGS. 4A through 4C can include fabrics having different coefficient of friction similar to the configuration of the object contact surface 110 and outside facing surface 108 of the garment 100 illustrated in FIGS. 1, 2A, and 2B.

The garment 200 can function as a full-length compression arm sleeve. The elbow pad 208 can include closed cell foam or other suitable padding. The strips 210 can include silicone rubber, or other suitable materials to increase the coefficient of friction of the object contact surface 202 compared to the coefficient of friction of the remainder 204 of the exterior surface.

The strips 210 can be raised from the fabric of the garment 200, or otherwise configured, such that an object coming into contact with the object contact surface 202 primarily engages the strips 210. The strips 210 can be angled inward to encourage an incoming pass of a sports ball (e.g. football or rugby ball) to be brought to the wearer's body. The strips 210 can have a similar texture to silicone rubber material blends used in current American National Football League (NFL™) wide receiver gloves. The strips 210 can be added to the object contact surface 102 of the garment 100 illustrated in FIGS. 1, 2A, and 2B to enhance grip of the object contact surface 102.

The garment 200 illustrated in FIGS. 4A through 4C can be worn similar to the garment 100 illustrated in FIGS. 1, 2A, and 2B to carry objects or inside out so that the object contact surface 202 inhibits movement of the garment 200 against the wearer's skin. The garment 200 can additionally include features of an example garment described herein-above that are not specifically illustrated in FIGS. 4A through 4C. Such features can be incorporated into the garment 200 as understood by a person skilled in the pertinent art.

The elbow pad 208 illustrated in FIGS. 4B and 4C can be added to the garment 100 illustrated in FIGS. 1, 2A, and 2B. A closed cell foam allows for high energy absorption while using a minimal amount of padding. Closed cell foams can be made of many materials but are commonly made from polyethylene. Low-density polyethylene foam (LDPE) has a low Young's modulus and low density. This allows the foam to return to its original shape following an impact, which can be effective to maintain energy absorption properties of the material. The closed-cell foam pad on the elbow can be fractured into small pieces to increase athlete comfort. By fracturing the pad, multiple flex points are formed along the elbow area; this can allow the athlete to have free range of motion and provide protection in sensitive areas around the elbow. The elbow pad 208 can additionally, or alternatively include padding other than closed cell foam and/or a pocket into which padding can be inserted. For instance, the fabric in the region of the elbow pad 208 can be thicker than the fabric in the majority of the garment. A garment shaped to be worn elsewhere on the body can include a similarly constructed pad to protect shoulders, knees, wrists, hips, neck, ankles, etc.

The garment 200 can include surfaces with sufficiently high friction against skin on the interior, skin facing, surface of the tube to prevent the garment 200 from undesirably slipping out of position on the wearer's body. For instance, the garment 200 can include bands of elastic or silicone rubber material near each opening 112, 114 on the interior surface of the tube to resist slippage of the garment 200 against the wearer's skin when worn.

Currently, many sports leagues and associations (e.g. NFL™ and National Collegiate Athletic Association, NCAA™) prohibit adhesive materials on clothing or equipment for American football and other sports. The garments 100, 200 described herein can include rules-compliant materials to achieve the desired surface properties.

The materials used in the garments 100, 200 illustrated and otherwise described herein and variations thereof can be selected to facilitate proper function as well as athlete comfort. Particularly at higher levels of play, an athlete will not use a product if it is uncomfortable or not aesthetically pleasing. In general, materials used in compression garments have desirably low density, low Young's modulus, low cost, high yield strength, and high tensile strength. High yield strength and tensile strength can be effective to avoid material failure when the garment is stretched or pulled. A low Young's modulus can be effective to allow the material to be flexible to conform to the shape of the wearer's body. Both polyurethane (spandex) and polyamide (nylon) have desired characteristics as materials for a compression garment. Polyurethane provides a desirably low Young's modulus while polyamide provides desirably high yield strength and tensile strength. Polyamide provides structural integrity for the garment 100, 200, air and moisture permeability, and low heat retention for cooling while polyurethane provides compression to increase blood flow to the arm and effectively minimize swelling and soreness and also enables the garment 100, 200 the ability to return to a consistent relaxed form once stretched.

Choice of the materials in the garments 100, 200 can also affect surface properties of garment fabrics. Referring again to FIGS. 1, 2A, and 2B, the garment 100 can include fabrics with differing material composition so that the object contact surface 102 has a higher coefficient of friction compared to the outside facing surface 104. A fabric in the object contact surface 102 can include higher density of polyester and/or silicone composite while a fabric in the outside facing surface 104 can include higher density of polyurethane, polyamide, and/or polypropylene. In one example, the garment can include a blend of approximately 80% spandex and approximately 20% polyester on the outside facing surface and a blend of approximately 80% polyester and approximately 20% spandex on the object contact surface. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 80%" may refer to the range of values from 70% to 90% and "about 20%" may refer to the ranges of values from 10% to 30%. For designs with higher tolerance, "about" or "approximately" may refer to the range of values ±20% of the recited value.

Generally, a fabric that is substantially a blend of polyester and spandex can include a ratio of greater polyester to spandex on the object contact surface to achieve greater grip and a ratio of greater spandex to polyester on the outside facing surface to provide stretch to the garment and a smoother surface. The blends on the outside facing surface versus the object contact surface need not be inverse of each other as in the above example and various combinations can be suitable to meet the needs of various uses including those described herein. In one example, the garment can include a blend of approximately 90% spandex and approximately 10% polyester on the outside facing surface. In another example, the garment can include a blend of approximately 80% spandex and approximately 20% polyester on the outside facing surface. In another example, the garment can include a blend of approximately 70% spandex and approximately 30% polyester on the outside facing surface. In another example, the garment can include a blend of approximately 60% spandex and approximately 40% polyester on the outside facing surface. In one example, the garment can include a blend of 90% polyester and approximately 10% spandex on the object contact surface. In another example, the garment can include a blend of 80% polyester and approximately 20% spandex on the outside facing surface. In another example, the garment can include a blend of 70% polyester and approximately 30% spandex on the outside facing surface. In another example, the garment can include a blend of 60% polyester and approximately 40% spandex on the outside facing surface.

Geometry of fibers and weave/knit of the fabric can also affect surface properties, compression, comfort, aesthetics, cooling, and other functionality of the garment 100, 200. For instance, a seamlessly knitted triangular hollow nylon, and can be knitted with a weft-plain knitting weave to provide desirable moisture-wicking, low heat retention, and high air permeability.

Figure 5A:
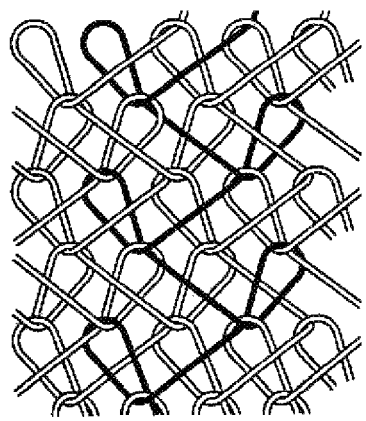
FIGS. 5A through 5D are illustrations of example knit structures according to aspects of the present invention.
Figure 5B:
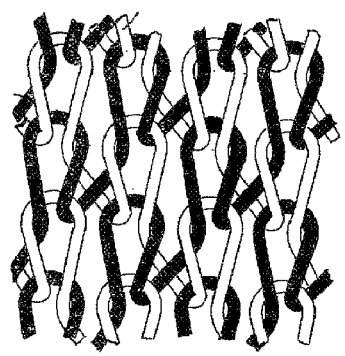
Figure 5C:
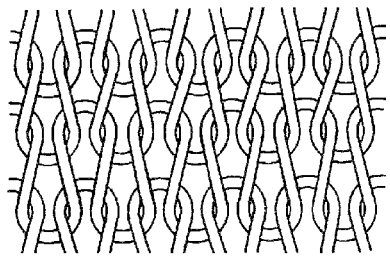
Figure 5D:
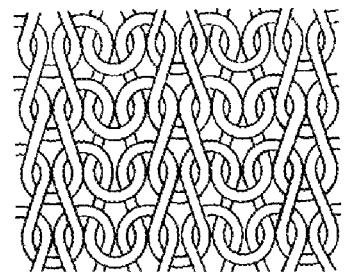

FIGS. 5A through 5D are illustrations of example knit structures. Although the garments 100, 200 illustrated and described herein (and variations thereof) can be constructed from woven fabrics, knitted fabrics can generally provide greater stretch and are therefore preferred. FIG. 5A is an example of a warp knit. FIG. 5B is an example of a hybrid warp-weft knit. FIGS. 5C and 5D are examples of weft knits. Variations of knitted structures are too numerous to illustrate, and many more can be used to achieve desired properties of fabrics for the example garments 100, 200 described herein and variations thereof.

Knitted techniques which include individually and simultaneously knitting two or more individual yarns can also be incorporated (e.g. double knitting, fair isle knitting, etc.). Double knitting typically is weft knit in a double layered stockinette pattern using two yarns that produces a double thick fabric with knit sides of each fabric layer facing outward, purl sides of each fabric layer together, and where visible patterns on opposite sides are negative images of each other. Fair isle knitting is typically weft knit in a stockinette pattern with two or more yarns in a single layer where yarns not used for a stitch are carried along rows of a purl side of the fabric and an image is visible on the knit side of the fabric. Resulting patterns from multiple-yarn knitting techniques are jacquard patterns. When using yarns having differing material blends, the resulting jacquard pattern can affect coefficient of friction of fabric surfaces. The yarns can also be dyed so that the resulting jacquard pattern provides a readily visible pattern. Additionally, or alternatively, a jacquard pattern based on texture can be knitted into a fabric by any of a number of knitting techniques too numerous to list such as selectively positioning knit and purl stitches, cabling, alternating increase/decrease stitches, slipping stitches across rows, etc. A textured jacquard pattern can affect coefficient of friction of fabric surfaces.

In some examples, the knit pattern can be selected to affect the smoothness or comparative coefficient of friction of the surfaces of the garment. For instance, the object contact surface 102 and the outside facing surface 104 can have differing knit patterns to contribute to their differing coefficient of friction. In some examples, the object contact surface 102 can have a 3-D textured knitted surface that has a greater coefficient of friction than the outside facing surface 104.

The knitted structures illustrated in FIGS. 5A, 5B, and 5C produce a fabric that has different fiber patterns on either side of the fabric. In some examples, the difference in fiber patterns can result in a higher coefficient of friction on one side of the fabric compared to the other. The knitted structure in FIG. 5D is a rib stitch that has similar fiber patterns on either side of the fabric and therefore has coefficients of friction on either side that are about equal to each other. The knit and purl patterns of each fabric can further be tailored to provide a jacquard pattern to display an illustration such as text, numbers, a logo, a random pattern, or a periodic pattern such as a honeycomb pattern.

Referring to FIG. 3, the garment 100 can be knit (or woven) such that the exterior surface S1 has a higher coefficient of friction than the interior surface S2 or vice versa. Referring to FIGS. 1 and 2A, the fabric of the garment 100 spanning the object contact surface 102 can be knit or woven such that the object contact surface 102 (being the exterior surface S1 in FIG. 3) can have a higher coefficient of friction compared to an interior surface S2 of the fabric under the object contact surface 102. For instance, the garment 100 can include a warp knit fabric (e.g. as in FIG. 5A or variation thereof) that includes the object contact surface 102 on the exterior of the garment 100 that has a different fiber pattern than on the interior of the garment 100 under the object contact surface 102 to cause the interior of the fabric to have a lower coefficient of friction than the object contact surface 102. Configured as such, the garment 100 can be easy enough to don and doff while providing desirable grip on the object contact surface 102. Similarly, the outside facing surface 104 (being the exterior surface S1 in FIG. 3) can have a lower coefficient of friction compared to an interior surface S2 of the fabric under the outside facing surface 104. Configured as such, the garment 100 can provide grip against the wearer's skin to prevent slippage of the garment 100 when worn while also providing a smooth outside facing surface 104 to deflect objects.

Further, any of the textile surfaces can have a coefficient of friction that differs based on direction of travel over the surface, e.g. traveling across rows of a knitted fabric surface can result in a different coefficient of friction compared to traveling across columns of the same knitted fabric surface. Additionally, or alternatively, the garment can be constructed from two layers of fabric that are stitched, glued, ultrasonic welded, thermal welded, knitted (e.g. double layer knit), and or rely on friction to function together, where the differing layers provide differing coefficient of friction for the exterior surface S1 compared to interior surface S2. The differing layers can include other differing material properties as advantageous for the application, for instance an athletic sleeve can have an inner layer with enhanced moisture wicking properties.

Referring to FIGS. 1, 2A, and 2B, preferably, the garment 100 includes a knit fabric having differing fiber patterns on opposite sides of the fabric so that the object contact surface 102 has a higher coefficient of friction compared to the coefficient of friction of the interior surface under the object contact surface 102. Preferably, the difference in coefficient is significant enough to be observable in a crude test where a finger is moved across the object contact surface 102 then subsequently across the interior surface under the object contact surface 102 at a similar pressure and speed and a noticeable resistance to movement is observed when moving across the object contact surface 102 compared to the interior surface.

The above disclosure describes several variations of a garment including, but not limited to, variations in materials, variations in configuration of surfaces having differing smoothness or coefficient of friction, variations in construction methods (e.g. weaving, knitting, seam construction), variations in methods of wearing and use, etc. Additional variations may be apparent to a person skilled in the pertinent art upon reading the present disclosure. Variations understood to a person skilled in the pertinent art according to the teachings herein are intended to be covered in the scope of the claims which follow.

What is claimed is:

1. A garment comprising:
   a substantially tubular textile comprising an interior, an exterior, two open ends defining ends of the garment, a length extending from each of the open ends across the substantially tubular textile, and a circumference circumscribing the substantially tubular textile, wherein the substantially tubular textile comprises a cross-section completely defined by fiber-based textile material throughout the entire length;
   a first fiber-based textile surface on the exterior extending a majority of the length and over a first portion of the circumference, and having a uniform smoothness; and
   a second fiber-based textile surface extending a majority of the length and over a second portion of the circumference, the first textile surface comprising a higher coefficient of friction than the second textile surface; and
   a single layer knitted fabric comprising an exterior fiber pattern on the exterior of the substantially tubular textile that is different than an interior fiber pattern on the interior of the substantially tubular textile such that the first fiber-based textile surface consists essentially of the exterior fiber pattern, and such that the interior fiber pattern comprises a lower coefficient of friction than the exterior fiber pattern.

2. The garment of claim 1, wherein the first fiber-based textile surface, against a leather or polymeric ball, comprises a static coefficient of friction and/or kinetic coefficient of friction sufficient to inhibit the leather or polymeric ball from disengaging the first fiber-based textile surface when the first fiber-based textile surface is positioned on a forearm of an athlete and the athlete is carrying the leather or polymeric ball via compression to the first fiber-based textile surface.

3. The garment of claim 1, wherein the first fiber-based textile surface, against each of a wood surface, a metal surface, a plastic surface, a paper surface, and a cardboard surface of respective objects, comprises a static coefficient of friction and/or kinetic coefficient of friction sufficient to inhibit the respective objects from disengaging the first textile surface when the first fiber-based textile surface is positioned on a forearm of a human wearer is carrying the respective objects via compression to the first fiber-based textile surface.

4. The garment of claim 1, being a compression garment and comprising sufficient flexibility to conform to the shape of a wearer's arm and configured to provide compression to the wearer's arm.

5. The garment of claim 1, being abrasion and cut resistant.

6. A garment comprising:
   a sleeve comprising an exterior, an interior, and a circumference, wherein the sleeve comprises a cross-section completely defined by fiber-based textile material throughout an entire length of the sleeve;
   a single layer knitted fabric extending over a first portion of the circumference and comprising a first fiber-based textile surface on the exterior of the single layer knitted fabric which extends over the first portion of the circumference and has a uniform smoothness, wherein the first fiber-based textile surface comprises an exterior fiber pattern that is different from an interior fiber pattern of the single layer knitted fabric on the interior of the sleeve, and wherein the interior fiber pattern comprises a lower coefficient of friction than the exterior fiber pattern; and
   a second fiber-based textile surface on the exterior of the sleeve and extending over a second portion of the circumference, opposite the first fiber-based textile surface, the first fiber-based textile surface having a coefficient of friction greater than a coefficient of friction of the second fiber-based textile surface.

7. The garment of claim 6, wherein the first fiber-based textile surface, against a leather or polymeric ball, comprises a static coefficient of friction and/or kinetic coefficient of friction sufficient to inhibit the leather or polymeric ball from disengaging the first fiber-based textile surface when the first fiber-based textile surface is positioned on a forearm of an athlete and the athlete is carrying the leather or polymeric ball via compression to the first textile surface.

8. The garment of claim 6, wherein the first fiber-based textile surface, against each of a wood surface, a metal surface, a plastic surface, a paper surface, and a cardboard surface of respective objects, comprises a static coefficient of friction and/or kinetic coefficient of friction sufficient to inhibit the respective objects from disengaging the first fiber-based textile surface when the first fiber-based textile surface is positioned on a forearm of a human wearer is carrying the respective objects via compression to the first fiber-based textile surface.

9. The garment of claim 6, being a compression garment and comprising sufficient flexibility to conform to the shape of a wearer's arm and configured to provide compression to the wearer's arm.

10. A tubular garment having a circumference, two open ends, and a length defined between and joining the two open ends, the tubular garment comprising:
  a first single layer knitted fabric portion extending over an entirety of the length and over approximately half of the circumference; and
  a second single layer knitted fabric portion extending over an entirety of the length and over approximately half of the circumference,
  wherein an exterior surface of the tubular garment comprises an exterior fiber pattern of the first single layer knitted fabric portion and an exterior fiber pattern of the second single layer knitted fabric portion, wherein the exterior surface of the tubular garment is entirely fiber-based over an entirety of the length and an entirety of the circumference, wherein the exterior fiber pattern of the first single layer knitted fabric portion comprises a higher coefficient of friction than the exterior fiber pattern of the second single layer knitted fabric portion, and wherein an interior surface of the tubular garment comprises an interior fiber pattern of the first single layer knitted fabric portion and an interior fiber pattern of the second single layer knitted fabric portion;
  wherein the exterior fiber pattern of the first single layer knitted fabric portion comprises a higher coefficient of friction than the interior fiber pattern of the first single layer knitted fabric portion; and
  the tubular garment comprising a cross-section completely defined by fiber-based textile material throughout at least a majority of the length.

11. The tubular garment of claim 10,
  wherein the interior surface comprises a first ring of silicone disposed approximate a first end of the two open ends,
  wherein the interior surface comprises a second ring of silicone disposed approximate a second end of the two open ends, and
  wherein the interior surface is entirely fiber based over the entirety of the length and the entirety of the circumference except for the first ring of silicone and the second ring of silicone.

12. The tubular garment of claim 10, further comprising:
  silicone disposed on the interior surface approximate each of the two open ends,
  wherein the cross-section of the tubular garment is completely defined by fiber-based textile material throughout the entirety of the length except for the silicone disposed on the interior surface approximate each of the two open ends.

\* \* \* \* \*